United States Patent [19]

Alker et al.

[11] Patent Number: 4,957,930
[45] Date of Patent: Sep. 18, 1990

[54] DIHYDROPYRIDINE DERIVATIVES

[75] Inventors: David Alker, Birchington; Peter E. Cross, Canterbury, both of England

[73] Assignee: Pfizer Inc., New York, N.Y.

[21] Appl. No.: 183,817

[22] Filed: Apr. 20, 1988

[30] Foreign Application Priority Data

Apr. 21, 1987 [GB] United Kingdom ............... 8709447

[51] Int. Cl.$^5$ ................. C07D 211/86; A61K 31/455
[52] U.S. Cl. .................................... 514/356; 514/333; 514/334; 514/343; 514/318; 514/252; 514/237.2; 546/321; 546/194; 546/256; 546/257; 546/281; 544/131; 544/365
[58] Field of Search ............... 546/257, 271, 274, 270, 546/283, 167, 256, 280, 321, 281, 194; 544/333, 131, 365; 514/356, 333, 334, 338, 340, 342, 343, 256, 233

[56] References Cited

U.S. PATENT DOCUMENTS 4,532,248 7/1985 Franckowiak et al. ............. 514/302
4,654,353 3/1987 Alker et al. ......................... 546/321

OTHER PUBLICATIONS

Burger Medicinal Chemistry 2nd Edition, 1960.
Merck Index, 9th edition, pp. 1047–1048.

Primary Examiner—Jane T. Fan
Attorney, Agent, or Firm—Peter C. Richardson; Paul H Ginsburg; Robert F. Sheyka

[57] ABSTRACT

Dihydropyridines having unsaturated side chains are disclosed. The compounds are useful anti-ischemic and antihypertensive agents.

7 Claims, No Drawings

DIHYDROPYRIDINE DERIVATIVES

BACKGROUND OF THE INVENTION

The present invention relates to certain dihydropyridines, specifically to certain 1,4-dihydropyridines having an unsaturated moiety i.e. an alkenylene or alkynylene group in the 2-position side chain, and derivatives thereof, which have utility as anti-ischaemic and antihypertensive agents.

The compounds of the invention reduce the movement of calcium into the cell and they are thus able to delay or prevent the cardiac contracture which is believed to be caused by an accumulation of intracellular calcium under ischaemic conditions. Excessive calcium influx during ischaemia can have a number of additional adverse effects which would further compromise the ischaemic myocardium. These include less efficient use of oxygen for ATP production, activation of mitochondrial fatty acid oxidation and possibly, promotion of cell necrosis. Thus the compounds are useful in the treatment of prevention of a variety of cardiac conditions, such as angina pectoris, cardiac arrhythmias, heart attacks and cardiac hypertrophy. The compounds also have vasodilator activity since they can inhibit calcium influx in cells of vascular tissue and they are thus also useful as antihypertensive agents and for the treatment of coronary vasospasm.

SUMMARY OF THE INVENTION

According to the present invention there are provided 1,4-dihydropyridines of the formula (I):

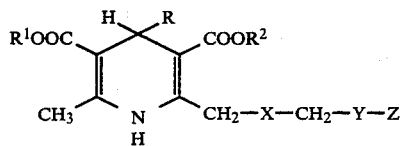
(I)

or pharmaceutically acceptable acid addition salts thereof: where
R is an optionally substituted aryl or heteroaryl group;
$R^1$ and $R^2$ are each independently $C_1-C_4$ alkyl or 2-methoxyethyl;
X is O or S
Y is —CH=CH— or —C≡C—; and
Z is —CHR$^5$OH where R$^5$ is H, $C_1-C_4$ alkyl or aryl; —CONH$_2$; —CO$_2$R$^6$ where R$^6$ is H or $C_1-C_4$ alkyl;

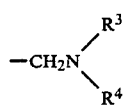

where $R^3$ and $R^4$ are each independently H or $C_1-C_4$ alkyl; or $R^3$ and $R^4$ taken together with the nitrogen atom to which they are attached form a 5 or 6 membered-ring optionally containing one or more further heteroatoms selected from N, O or S; provided that when Y is —C≡C—, Z is not CO$_2$(C$_1$-C$_4$) alkyl.

Compounds of formula (I) in which Y is —C≡C— and Z is CO$_2$(C$_1$-C$_4$) alkyl are disclosed in our copending European patent application publication No. 161917 as intermediates only.

The term "aryl" as used in this specification includes unsubstituted phenyl and phenyl substituted by, for example, one or two substituents each independently selected from nitro, halo, $C_1-C_4$ alkyl, $C_1-C_4$ alkoxy, hydroxy, trifluoromethyl and cyano. It also includes 1- and 2-naphthyl.

"Halo" means F, Cl, Br or I.

The term "heteroaryl" as used in this specification for R means an aromatic heterocyclic group which may optionally be substituted and includes, for example, benzofuranyl; benzothienyl; pyridyl optionally substituted by methyl, methylthio, halo or cyano; quinolyl; benzoxazolyl; benzothiazolyl; furyl; pyrimidinyl; thiazolyl; 2,1,3-benzoxadiazol-4-yl; 2,1,3-benzothiadiazol-4-yl; and thienyl optionally monosubstituted by halo or $C_1-C_4$ alkyl.

Alkyl and alkoxy groups having 3 or more carbon atoms can be straight or branched chain.

R is preferably phenyl substituted by 1 or 2 substituents selected from halo and CF$_3$, or is 2-chloropyrid-3-yl. R is most preferably 2-chlorophenyl or 2,3-dichlorophenyl.

$R^1$ and $R^2$ are preferably CH$_3$ or C$_2$H$_5$.

Most preferably, $R^1$ is CH$_3$ and $R^2$ is C$_2$H$_5$, or $R^1$ and $R^2$ are both CH$_3$.

X is most preferably O.

When Z is —CHR$^5$OH R$^5$ is preferably phenyl, n-butyl or hydrogen. Alternatively in those compounds in which Z is —CO$_2$R$^6$ R$^6$ is preferably H. When Z is

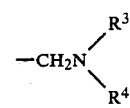

$R^3$ and $R^4$ are preferably both methyl; and when $R^3$ and $R^4$ are taken together with the nitrogen atom to which they are attached they preferably form a pyrrolidinyl, piperidino, morpholino, piperazinyl or N(C$_1$-C$_4$ alkyl)-piperazinyl group.

The compounds of the formula (I) containing one or more asymmetric centres will exist as one or more pairs of enantiomers, and such pairs or individual isomers may be separable by physical methods, e.g. by fractional crystallisation or chromatography of the parent compounds or suitable derivatives thereof as will be known to those skilled in the art. The invention includes the separated pairs as well as mixtures thereof, as racemic mixtures or as separated optically-active isomeric forms.

The pharmaceutically acceptable acid addition salts of the compounds of the formula (I) are those formed from acids which form non-toxic acid addition salts, for example the hydrochloride, hydrobromide, sulphate or bisulphate, phosphate or acid phosphate, acetate, citrate, fumarate, gluconate, lactate, maleate, succinate, mesylate and tartrate salts.

DETAILED DESCRIPTION OF THE INVENTION

The compounds of formula (I):

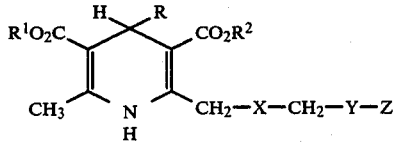

may be prepared by a number of routes. For example the alkyne of formula (II):

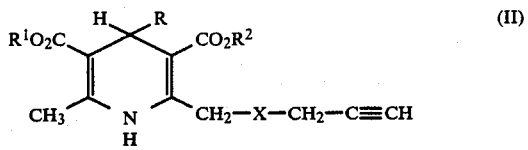

wherein R, $R^1$, $R^2$ and X are all as previously defined, may be reacted with carbon dioxide, aldehydes of the formula $R^5CHO$ or compounds of the formula

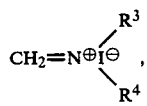

wherein $R^3$, $R^4$ and $R^5$ are as previously defined, in a suitable solvent in the presence of a strong base such as an n-alkyllithium, sodium hydride, or potassium hydroxide to give a compound of formula I where Z is —$CHR^5OH$, —$CO_2H$ or

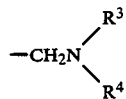

and Y is —C≡C—. A preferred base is n-butyl lithium. Ideal solvents include any inert solvent such as tetrahydrofuran, diethyl ether or dioxan. The most preferred solvent is tetrahydrofuran.

Compounds of formula (I) in which Y is —CH═CH— can be prepared by partial hydrogenation of those compounds of formula (I) in which Y is —C≡C—. Hydrogenation is preferably carried out over a palladium catalyst in a solvent such as pyridine.

Compounds of formula (I) in which Z is —$CONH_2$ or —$CO_2R^6$ can be prepared from compounds of formula (I) in which Z is —COOH by reaction with ammonia or by conventional esterification procedures, respectively.

Alternatively, compounds of formula (I) in which Z is a —$CONH_2$ group may be prepared by reaction of a compound of formula (III) with ammonia:

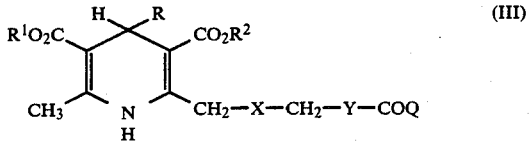

wherein R, $R^1$, $R^2$ and X are as previously defined and Q is a good leaving group; Q may be, for example, chloro or methoxy. The preparation of starting materials of formulae (II) and (III) is described in European patent application No. 85303304 (publication No. 161917) and is illustrated in Preparations 1 and 2, respectively, of this application.

The ability of the compounds to inhibit the movement of calcium into the cell is shown by their effectiveness in reducing the contraction of vascular tissue in vitro which is the consequence of calcium influx caused by high extracellular concentration of potassium ions. The test is performed by mounting spirally cut strips of rat aorta with one end fixed and the other attached to a force transducer. The tissue is immersed in a both of physiological saline solution containing 2.5 mM $Ca^{2+}$ and 5.9 mM $K^+$. Potassium chloride is added to the bath with a pipette to give a final $K^\oplus$ concentration of 45 millimolar. The change in tension caused by the resulting contraction of the tissue is noted. The bath is drained and replaced with fresh saline solution and, after 45 minutes, the test is repeated with the particular compound under test present in the saline solution. The concentration of compound required to reduce the response by 50% ($IC_{50}$) is recorded.

The antihypertensive activity of the compounds is evaluated after oral administration by measuring the fall in blood pressure in spontaneously hypertensive rats or renally hypertensive dogs.

For administration to man in the curative or prophylactic treatment of cardiac conditions and hypertension, oral dosages of the compounds will be in the range of from 5–1000 mg daily for an average adult patient (70 mg), typically 10–60 mg daily. Thus for a typical adult patient, individual tablets or capsules will generally contain 5, 10 or 20 mg of active compound, in a suitable pharmaceutically acceptable vehicle or carrier. Dosages for intravenous administration will typically be within the range 1 to 10 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic.

Thus in a further aspect the invention provides a pharmaceutical composition comprising a compound of the formula (I), including compounds in which Y is —C≡C— and Z is $CO_2(C_1$-$C_4)$alkyl, or a pharmaceutically acceptable salt thereof, together with a pharmaceutically acceptable diluent or carrier.

The invention also includes a compound of the formula (I), including compounds in which Y is —C≡C— and Z is $CO_2(C_1$-$C_4)$alkyl, or a pharmaceutically acceptable salt thereof, for use in medicine, in particular in the treatment of ischaemic heart disease, angina, or hypertension in a human being.

The invention also provides a method of protecting the heart from the deleterious effects of ischaemia, which comprises administering an effective amount of a compound of the formula (I), including compounds in which Y is —C≡C— and Z is $CO_2(C_1-C_4)$alkyl, or pharmaceutically acceptable salt thereof, or a pharmaceutical composition as defined above.

The invention also includes a method of treating hypertension which comprises administering an antihypertensive amount of a compound of the formula (I), including compounds in which Y is —C≡C— and Z is $CO_2(C_1-C_4)$alkyl, or pharmaceutically acceptable salt thereof, or pharmaceutical composition as defined above.

EXAMPLE 1

4-{[4-(2,3-Dichlorophenyl)-3-ethoxycarbonyl-5-methoxycarbonyl-6-methyl-1,4-dihydropyrid-2-yl]-methoxy}-1-hydroxy-1-phenylbut-2-yne A 1.6M solution of n-butyllithium in hexane (3.4 ml) was added dropwise over 15 minutes to a stirred, cooled (acetone/cardice bath) solution of 1-{[4-(2,3-dichlorophenyl)-3-ethoxycarbonyl-5-methoxycarbonyl-6-methyl-1,4-dihydropyrid-2-yl]methoxy}prop-2-yne (1.10 g) in tetrahydrofuran (25 ml) and the mixture stirred at −70° for 2 hours. The mixture was then allowed to warm up to between −35° and −40°, stirred at that temperature for 2 hours, treated dropwise with a solution of benzaldehyde (0.16 g) in tetrahydrofuran (5 ml) over 5 minutes and then stirred at between −10° and −15° for one hour and at room temperature for 14 hours. The reaction mixture was partitioned between ethyl acetate and water and the organic layer washed with water, dried over $Na_2SO_4$ and evaporated. The residue was triturated with diethyl ether and the resulting solid collected, washed with diethyl ether and dried to give the title compound (0.18 g), m.p. 160°–164°.

Analysis %: Found: C, 61.79; H, 5.12; N, 2.61; $C_{28}H_{27}Cl_2NO_6$ requires: C, 61.76; H, 4.96; N, 2.57.

EXAMPLES 2 AND 3

4-{[4-(2,3-Dichlorophenyl)-3-ethoxycarbonyl-5-methoxycarbonyl-6-methyl-1,4-dihydropyrid-2-yl]methoxy}-1-dimethylaminobut-2-yne and 1-{[4-(2,3-dichlorophenyl)-3-ethoxycarbonyl-5-methoxycarbonyl-6-methyl-1,4-dihydropyrid-2-yl]methoxy}-4-hydroxyoct-2-yne A 2.6M solution of n-butyllithium in hexane (13.2 ml) was added dropwise to a stirred, cooled (acetone/cardice bath) solution of 1-{[4-(2,3-dichlorophenyl)-3-ethoxycarbonyl-5-methoxycarbonyl-6-methyl-1,4-dihydropyrid-2-yl]methoxy}prop-2-yne (7.0 g) in tetrahydrofuran (50 ml) and the mixture allowed to warm up to −10° over 15 minutes, cooled to −70° and treated with N,N-dimethylmethyleneammonium iodide (Eschenmoser's salt) (2.96 g) in one batch as a finely ground powder. The mixture was allowed to warm up to 4° over 30 minutes, stirred at 4° for one hour and then quenched into a mixture of saturated aqueous sodium hydrogen carbonate and dichloromethane. The layers were separated and the organic layer washed three times with water, dried over $MgSO_4$ and evaporated. The residue was separated by chromatography on $SiO_2$ (25 g) using hexane plus 40% ethyl acetate followed by hexane:ethyl acetate:diethylamine=85:15:4 as eluant. Appropriate fractions were combined and evaporated:

(i) The less polar material gave the first title compound (4.5 g) as an oil.

Analysis %: Found: C, 58.13; H, 5.97; N, 5.38; $C_{24}H_{28}Cl_2N_2O_5$ requires: C, 58.19; H, 5.70; N, 5.65.

(ii) The more polar material was recrystallised from isopropanol to give the second title compound (0.24 g), m.p. 134°–138°.

Analysis %: Found: C, 59.41; H, 6.03; N, 2.59; $C_{26}H_{31}Cl_2NO_6$: C, 59.55; H, 5.96; N, 2.67.

EXAMPLE 4

4-{[4-(2,3-Dichlorophenyl)-3-ethoxycarbonyl-5-methoxycarbonyl-6-methyl-1,4-dihydropyrid-2-yl]methoxy}-1-hydroxybut-2-yne A 2.6M solution of n-butyllithium in hexane (1.7 ml) was added dropwise to a stirred, cooled (acetone/cardice bath) solution of 1-{[4-(2,3-dichlorophenyl)-3-ethoxycarbonyl-5-methoxycarbonyl-6-methyl-1,4-dihydropyrid-2-yl]methoxy}prop-2-yne (0.88 g) in tetrahydrofuran (30 ml) and the mixture allowed to warm up to −20° over 15 minutes and maintained at that temperature for one hour. A stream of gaseous formaldehyde (produced by heating (4-tert-butylcyclohexyloxy)methanol (5 g) at 160° in a stream of nitrogen) was passed through the reaction mixture at −20° and the mixture stirred at room temperature for 45 minutes and evaporated. The residue was partitioned between ethyl acetate and 5% aqueous sodium carbonate solution and the organic layer washed three times with water, dried over $MgSO_4$ and evaporated. The residue was purified by chromatography on $SiO_2$ (20 g) using hexane plus 0–50% ethyl acetate as eluant to give the title compound (85 mg) as an oil.

Analysis %: Found: C, 56.44; H, 5.27; N, 2.91; $C_{22}H_{23}Cl_2NO_6$ requires: C, 56.41; H, 4.91; N, 2.99.

EXAMPLE 5

4-{[4-(2,3-Dichlorophenyl)-3-ethoxycarbonyl-5-methoxycarbonyl-6-methyl-1,4-dihydropyrid-2-yl]methoxy}-2-butynamide A mixture of ethyl 4-{[4-(2,3-dichlorophenyl)-3-ethoxycarbonyl-5-methoxycarbonyl-6-methyl-1,4-dihydropyrid-2-yl]methoxy}-2-butynoate (3.00 g), 0.880 aqueous ammonia (10 ml) and dioxane (10 ml) was shaken vigorously for 1.5 hours and then partitioned between ethyl acetate and water. The aqueous layer was extracted into ethyl acetate and the combined ethyl acetate layers were washed with water, dried over $Na_2SO_4$ and evaporated. The residue was purified by chromatography on $SiO_2$ (25 g) using dichloromethane plus 0–30% ethyl acetate as eluant. Appropriate fractions were combined and evaporated and the residue triturated with diethyl ether. The resulting solid was collected, washed with diethyl ether and dried to give the title compound (0.41 g), m.p. 147°–148°.

Analysis %: Found: C, 54.58; H, 4.78; N, 5.67 $C_{22}H_{22}Cl_2N_2O_6$ requires: C, 54.90; H, 4.61; N, 5.82.

EXAMPLE 6

4-{[4-(2,3-Dichlorophenyl)-3-ethoxycarbonyl-5-methoxycarbonyl-6-methyl-1,4-dihydropyrid-2-yl]methoxy}-1-dimethylaminobut-(2Z)-ene A solution of 4-{[4-(2,3-dichlorophenyl)-3-ethoxycarbonyl-5-methoxycarbonyl-6-methyl-1,4-dihydropyrid- 2-yl]methoxy}-1-dimethylaminobut-2-yne (1.10 g) in pyridine (75 ml) was stirred at room temperature in the presence of 5% palladium on calcium carbonate under one atmosphere of hydrogen for 45 minutes. The mixture was evaporated and the residue twice taken up in toluene and evaporated. The residue was purified by chromatography on SiO₂ (20 g) using dichloromethane plus 1–5% of 10% 0.880 aqueous ammonia in methanol as eluant. Appropriate fractions were combined and evaporated. The residue was dissolved in methanol (20 ml) and the solution treated with fumaric acid (74 mg). The mixture was then evaporated and the residue crystallised from ethyl acetate to give the fumarate salt of the title compound (0.195 g) as a hemihydrate, m.p. 142°–146°.

Analysis %: Found: C, 53.90; H, 5.54; N, 4.44; C₂₄H₃₀Cl₂N₂O₅.C₄H₄O₄.0.5H₂O requires: C, 54.02; H, 5.67; N, 4.50.

EXAMPLE 7

4-{[4-(2,3-Dichlorophenyl)-3-ethoxycarbonyl-5-methoxycarbonyl-6-methyl-1,4-dihydropyrid-2-yl]methoxy}-2-butynoic acid A 1.6M solution of n-butyllithium in hexane (36 ml) was added dropwise over 40 minutes to a stirred, cooled (acetone/cardice bath) solution of 1-{[4-(2,3-dichlorophenyl)-3-ethoxycarbonyl-5-methoxycarbonyl-6-methyl-1,4-dihydropyrid-2-yl]methoxy}prop-2-yne (11.0 g) in tetrahydrofuran (110 ml) and the mixture allowed to warm to −40° over one hour. The mixture was then cooled to −60° and carbon dioxide bubbled through the stirred solution at that temperature for one hour. Carbon dioxide was then bubbled through the mixture for a further one hour whilst it was allowed to warm up to 0°. The mixture was then diluted with water (100 ml) and the layers separated. The aqueous layer was washed with diethyl ether, acidified to pH 1.0 with concentrated hydrochloric acid and extracted into dichloromethane. The combined dichloromethane extracts were dried over MgSO₄ and evaporated and the residue triturated with methanol. The resulting solid was collected, washed with methanol and dried to give the title compound (8.87 g) as a hemihydrate containing half a mole of methanol of crystallisation, m.p. 100°.

Analysis %: Found: C, 53.32; H, 4.93; N, 2.74; C₂₂H₂₁Cl₂NO₇.0.5H₂O.0.5CH₃OH requires: C, 53.26; H, 4.73; N, 2.76.

EXAMPLE 8

Ethyl 4-{[4-(2,3-Dichlorophenyl)-3-ethoxycarbonyl-5-methoxycarbonyl-6-methyl-1,4-dihydropyrid-2-yl]methoxy}-2-butynoate A solution of 4-{[4-(2,3-dichlorophenyl)-3-ethoxycarbonyl-5-methoxycarbonyl-6-methyl-1,4-dihydropyrid-2-yl]methoxy}-2-butynoic acid (2.50 g), benzyltrimethylammonium hydroxide (0.87 g) and ethyl bromide (0.62 g) in dimethyl sulphoxide (5 ml) was stirred at room temperature for 48 hours, quenched into water and extracted twice into ethyl acetate. The combined ethyl acetate extracts were washed with water, dried over MgSO₄ and evaporated. The residue was crystallised from methanol to give the title compound (2.22 g), m.p. 123°–125°.

¹H-n.m.r. (CDCl₃) δ=7.26 (1H, dd, J=8 and 2 Hz), 7.20 (1H, dd, J=8 and 2 Hz), 7.03 (1H, t, J=8 Hz), 5.41 (1H, s), 4.76 (2H, AB, J=14 Hz), 4.40 (2H, s), 4.20 (2H, q, J=7 Hz), 3.99 (2H, q, J=7 Hz), 3.58 (3H, s), 2.32 (3H, s), 1.25 (3H, t, J=7 Hz) and 1.14 (3H, t, J=7 Hz).

PREPARATION 1

1-{[4-(2,3-Dichlorophenyl)-3-ethoxycarbonyl-5-methoxycarbonyl-6-methyl-1,4-dihydropyrid-2-yl]methoxy}-2-propyne

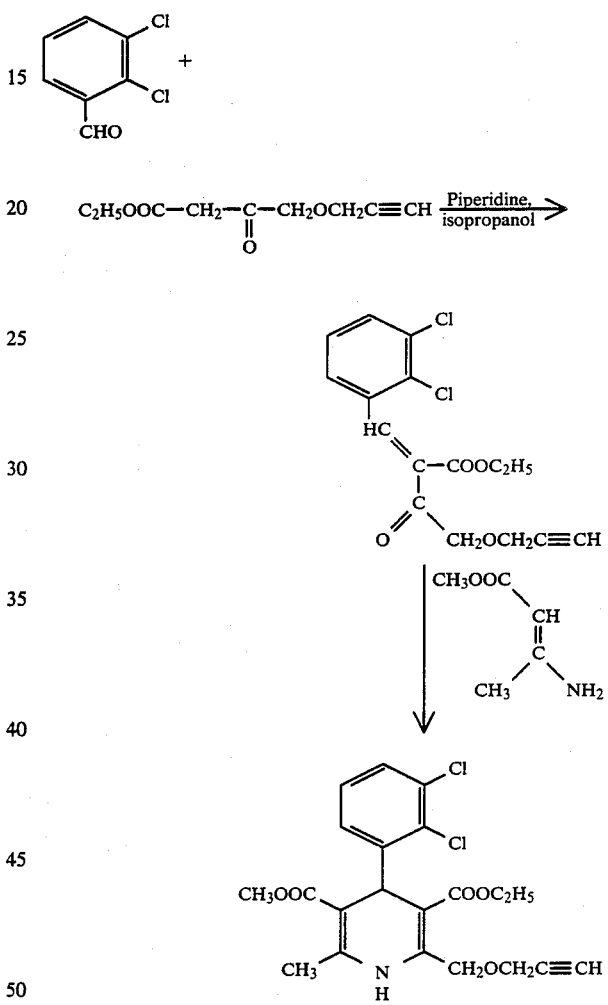

Piperidine (2.4 g) was added dropwise over 10 minutes to a stirred mixture of ethyl 4-(prop-2-ynoxy)acetoacetate (63 g) and 2,3-dichlorobenzaldehyde (60 g) in isopropanol (600 ml) and the mixture was stirred at room temperature for 24 hours. The mixture was then treated with methyl 3-aminocrotonate (39 g), stirred at room temperature for four days and evaporated. The residual oil was dissolved in methanol (300 ml) and the solution kept at −20° for two days. The resulting solid was collected, washed with cold methanol and dried to give the title compound (29.5 g), m.p. 104°–105°, which was used directly.

PREPARATION 2

Methyl 4-{[4-(2,3-dichlorophenyl)-3-ethoxycarbonyl-5-methoxycarbonyl-6-methyl-1,4-dihydropyrid-2-yl]methoxy}but-2-ynoate

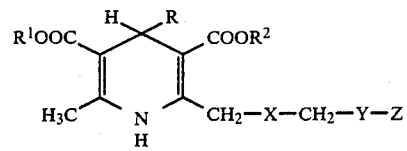

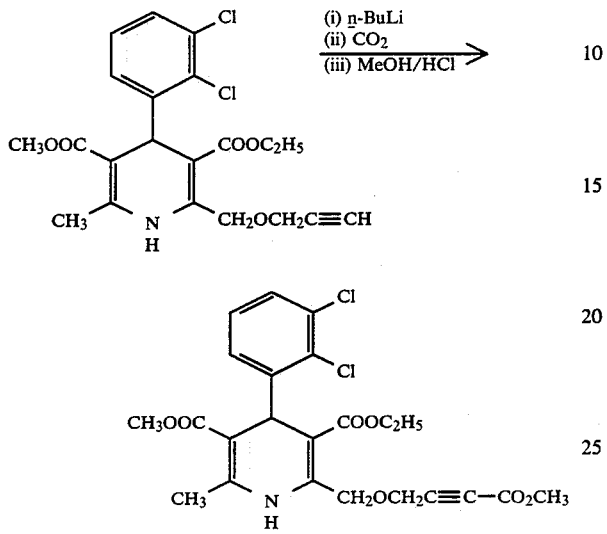

A 1.6M solution of n-butyllithium in hexane (45 ml) was added dropwise to a solution of 1-{[4-(2,3-dichlorophenyl)-3-ethoxycarbonyl-5-methoxycarbonyl-6-methyl-1,4-dihydropyrid-2-yl]methoxy}-2-propyne (132 g) in tetrahydrofuran (1 l.) keeping the temperature below −40°. The mixture was stirred at −60° for 2 hours and then carbon dioxide gas was passed through the solution for 30 minutes with cooling in an acetone/cardice bath. The mixture was allowed to warm to 0° while the passage of carbon dioxide gas was continued and then quenched with water (1 l.) and the layers separated. The aqueous layer was extracted into ether (500 ml) and the combined organic layers were washed with water, diluted with dichloromethane, washed with 1M HCl, dried over MgSO4 and evaporated. The residue was triturated with methanol and the resulting solid collected, washed with cold (−20°) methanol and dried to give 4-{[4-(2,3-dichlorophenyl)-3-ethoxycarbonyl-5-methoxycarbonyl-6-methyl-1,4-dihydropyrid-2-yl]methoxy}but-2-ynoic acid, (83.7 g), m.p. 150°–152°.

A mixture of this crude acid (14 g) and concentrated hydrochloric acid (1 ml) in methanol (100 ml) was heated under reflux for 2 hours, concentrated to a volume of 50 ml and diluted with water (140 ml) and chloroform (140 ml). The layers were separated and the organic layer was washed with water, dried over Na2SO4 and evaporated. The residue was triturated with hot methanol and, after cooling, the resulting solid was collected, washed with methanol and dried to give the title ester, (9.0 g), m.p. 111°–113°.

We claim:

1. A compound of the formula $$R^1OOC \diagup \overset{H \diagup R}{\phantom{C}} \diagdown COOR^2$$
$$H_3C-\underset{H}{N}-CH_2-X-CH_2-Y-Z$$

or a pharmaceutically acceptable acid addition salt thereof where

R is selected from the group consisting of phenyl, phenyl substituted by one or two substituents selected from the group consisting of halo and $CF_3$, and 2-chloro-3-pyridyl;

$R^1$ and $R^2$ are each independently methyl or ethyl;

X is O or S;

Y is —CH=CH or —C≡C—;

and Z is $CHR^5OH$ wherein $R^5$ is H, n-butyl, or phenyl;

—$CO_2R^6$ where $R^6$ is H;

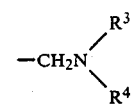

wherein $R^3$ and $R^4$ are each independently methyl; or when taken together with the N atom to which they are attached form a pyrrolidinyl, piperidino, morpholino, piperazinyl or $N(C_1-C_4)$alkyl piperazinyl group.

2. A compound according to claim 1 wherein $R^1$ and $R^2$ are each methyl or ethyl.

3. A compound according to claim 1 wherein when Z is $CHR^5OH$, $R^5$ is phenyl, n-butyl or hydrogen.

4. A compound according to claim 1 wherein when Z is $CHR^5OH$, $R^5$ is phenyl, n-butyl or hydrogen.

5. A compound according to claim 1 wherein when Z is $CHR^5OH$, $R^5$ is phenyl, n-butyl or hydrogen.

6. A pharmaceutical composition comprising a compound according to claim 1, in an amount effective for the treatment of ischaemia and hypertension, together with a pharmaceutically effective carrier or diluent.

7. A method for the treatment of ischaemia and hypertension comprising administering to a mammal in need of such treatment an effective amount of a compound according to claim 1.

* * * * *